United States Patent [19]

Mondadori

[11] Patent Number: 5,455,254
[45] Date of Patent: Oct. 3, 1995

[54] SUBSTITUTED BENZOFURANYLPIPERIDINE AS A NOOTROPIC AGENT

[76] Inventor: Cesare Mondadori, Traugott Meyer-Strasse 70, 4147 Aesch, Switzerland

[21] Appl. No.: 180,724

[22] Filed: Jan. 13, 1994

Related U.S. Application Data

[63] Continuation-in-part of Ser. No. 113,589, Aug. 27, 1993, abandoned, which is a continuation of Ser. No. 836,666, Feb. 14, 1992, abandoned.

[30] Foreign Application Priority Data

Feb. 15, 1991 [CH] Switzerland ............... 00470/91

[51] Int. Cl.$^6$ ............................................... A01N 43/40
[52] U.S. Cl. ............................................... 514/326
[58] Field of Search ................................. 514/326

[56] References Cited

U.S. PATENT DOCUMENTS

| | | | |
|---|---|---|---|
| 4,210,655 | 7/1980 | Schenker et al. | 514/646 |
| 4,600,719 | 7/1986 | Schenker et al. | 514/646 |
| 4,829,067 | 5/1989 | Iijima et al. | 514/646 |
| 4,971,995 | 11/1990 | Schoofs et al. | 514/646 |
| 4,977,159 | 12/1990 | Sevrin et al. | 514/646 |
| 4,999,382 | 3/1991 | Wurtman | 514/646 |
| 5,011,849 | 4/1991 | Gassner et al. | 514/646 |

FOREIGN PATENT DOCUMENTS

| | | |
|---|---|---|
| 1024034 | 3/1966 | United Kingdom . |
| 1565055 | 4/1990 | United Kingdom . |
| 8903692 | 5/1989 | WIPO . |

OTHER PUBLICATIONS

Chem. Abst. 109:143172 1988.
Chem. Abst. 106:4786 1986.
Chem Abst. 105:203054 1985.
Chem Abst. 111:225228r, 1989, "The Reversible MAO Inhibitor Brofaromine Inhibits Serotonin Uptake in Vivo".
Chem Abst. 115:201791a, 1991 "The Inhibition of Monoamine Oxidase by Brofaromine".
Chem Abst. 114:221228e, 1991 "Some Central Effects of Brofaromine Given Repeatedly are Phase Dependent".
Bieck, et al, J. Neural Transm 1989 [Suppl.] 28:21–31.
Am. J. Psychiatry 142, (1985) pp. 763–764 Abstract.
Schiwy et al, J. Neural Transm 1989 [Suppl.] 28;33–44.
Liebowitz et al; Arch. Gen Psychiatry 42, 729–736; Jul. 1985.
Liebowitz et al; Acta Psychiatr Scand. 1990:Suppl. 260:29–34.
Liebowitz, et al; J. Clin. Psychiatry 49:7 pp. 252–257; Jul. 1988.
Davidson et al; Arch Gen Psychiatry, Mar. 1990 pp. 259–266.
Silver et al; J. Clin Psychiatry 51:10 (Suppl) pp. 33–38 Oct. 1990.
Friedman; J. Traumatic Stress 41(1), 67–91, 1991.
Kyburz; Drug News Perspect 3(10), 592–599, Dec. 1990.
Tariot et al, Psychopharmacology 91(4) 489–495, 1987.
Drugs of the Future; Brofaromine; 10, No. 5, 371–373; 1985.
Nahunek et al; Act. Nerv. Super. 32(3), 230–231, 1990.
J. Neural Transm [P–D Sect] (1989) 1:82–83.
The Merck Index, 11th Ed. 1989, Piracetam Entry 7459, p. 1189.
Pharma Structures–4 Printout for CGS 5649B Sep. 1989.
Pharmastructures–4 Printout for Modobemide Jun. 1990.
Mondadori et al; Behavioral and Neural Biology 57, 149–156 (1992).
Derwent Atstr. BPS 22 32 35 60 91–07627 of Fund. Am. Clin. Pharmacol., No. 5, 588, 1990; Berlin et al.
Fawcett et al; Derwent Abstr. TS 32 35 64 91–25518 J. Clin Psychopharmacol. 11, No. 2, 127–132, 1991.
Derwent Abstr. TS 26 32 35 85–35035 or Jenike; Am. J. Psychiatry 142, No. 6, 763–64, 1985.
Derwent Abstr. 35 67 69 88–30603 of Small; J. Clin Psychiatry 49, No. 5, Suppl. 8–13, 1988.
Derwent Abstr. T 32 84–49695 of Jenike; J. Am. Geriatr. Soc. 32, No. 8, 571–575, 1984.
Linnoila et al; Acta Psychiatr. Scand., Suppl. 308 vol. 68, 175–181, 1983.
Weingartner et al; Science vol. 221, 427–474 (1983).
Warrington et al; Br. J. Clin. Pharmacol. (1984), 18, 549–557.
Curran et al; Psychopharmacology (1986) 89:360–363.
Curran et al; Psychopharmacology (1988) 95:520–527.
Saletu et al; J. Neural Transmission 49, 63–86 (1980).
Eckardt et al; 15th Collegium Internationale Neuro–Psychopharmacologicum, 1986, S–21, p. 55–57.
Martin et al; Arch Gen Psychiatry; vol. 46, 617–621 (Jul. 1989).
Moskowitz and Burns; Prog. Neuro–Psychopharmacol. and Biol. Psychiat. 1988, vol. 12, 783–792.
Ahlers and Best; Journal of Comparative and Psysiological Psychology, 1972, vol. 79, No. 3, 371–376.
Waldmeier and Stocklin, European Journal of Pharmacology vol. 169, Nos. 2/3, Oct. 10, 1989, 197–204.
Waldmeier and Stocklin; European Journal of Pharmacology (List continued on next page.)

Primary Examiner—Paul J. Killos
Attorney, Agent, or Firm—Irving M. Fishman; Karen G. Kaiser

[57] ABSTRACT

4-(7-Bromo-5-methoxybenzofuran-2-yl)piperidine (brofaromine) of formula I

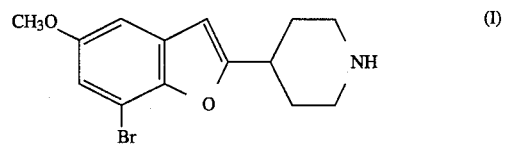

and its pharmaceutically acceptable salts can be used as active ingredients in medicaments for retarding the degeneration of nerve cells that accompanies degenerative nerve disorders, and as a nootropic agent for treating disorders that are responsive to treatment with nootropic agents.

5 Claims, No Drawings

OTHER PUBLICATIONS 180 (1990) 297–304.

Waldmeir et al; "Reversible Monoamine Oxidase Inhibition: Relation Between Effects on Enzymatic Activity Measured Ex14 Vivo and on Amine Metabolism" Monoamine Oxidase and Disease (American Press London 1984).

Mondadori et al; Psychopharmacology (1992) 109:383–389.

Mondadori et al; Clinical Neuropharmacology, vol. 9, Suppl. 3, pp. 527–538, 1986.

Mangoni et al; Drug Development Research 14:217–222 (1988).

Mondadori et al; Psychopharmacology (1992) 108:11–15.

Villardita et al; J. Neural Transm. (1987) [Suppl9 24:293–298.

Ban et al; Prog Neuro–Psychopharmacol. & Biol. Psychiat. 1990, vol. 14, pp. 525–551.

Davis et al; New England Journal of Medicine, vol. 327, No. 18, Oct. 29, 1992, pp. 1253–1259.

Harrell et al; Neurology 1990; 40:1350–1354.

Guillaumel et al; Eur. J. Med. Chem. –Chem Ther. 1983, vol. 18, No. 5, pp. 431–436.

Gueremy et al; J. Med. Chem 1980, 23, 1306–1310.

SUBSTITUTED BENZOFURANYLPIPERIDINE AS A NOOTROPIC AGENT

This is a continuation-in-part application of our copending patent application Ser. No. 8/113,589, filed Aug. 27, 1993 now abandoned which in turn is a continuation of our previous patent application Ser. No. 07/836,666, filed Feb. 14, 1992, now abandoned.

The invention relates to the use of 4-(7-bromo-5-methoxybenzofuran-2-yl)piperidine (brofaromine) of formula I

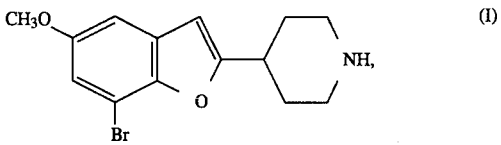

or of a pharmaceutically acceptable salt thereof, as an active ingredient in nootropic medicaments or for the preparation of a nootropic agent, to pharmaceutical compositions comprising the above, and to a method of retarding the degeneration of nerve cells that accompanies degenerative nerve disorders, such as Alzheimer's disease and Parkinson's disease, and of treating disorders that are responsive to treatment with nootropic agents.

Pharmaceutically acceptable salts of 4-(7-bromo-5-methoxybenzofuran-2-yl)piperidine (brofaromine) are especially its pharmaceutically acceptable salts with suitable mineral acids, such as hydrohalic acids, sulfuric acid or phosphoric acid, for example hydrochlorides, hydrobromides, sulhtes, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

4-(7-Bromo-5-methoxybenzofuran-2-yl)piperidine (brofaromine) and its pharmaceutically acceptable salts are known. When administered subcutaneously to rats in a dose ranging from approximately 10 to approximately 50 mg/kg, they inhibit the uptake of noradrenaline into the heart. When administered orally to rats, brofaromine selectively and reversibly inhibits monoamine oxidase A (MAO-A) with an $ED_{50}$ of 21 mg/kg (Waldmeier and Stöcklin, Eur. J. Pharmacol. Vol. 169, pages 197–204 (1989)). Brofaromine also inhibits 5-HT (serotonine) uptake, as measured by the synaptosome ex vivo model with an $ED_{50}$ about 30 times higher than that for the inhibition of MAO-A. Brofaromine and its phamaceutically acceptable salts have therefore been proposed as active ingredients for antidepressant medicaments for the treatment of depression, and have been shown to be clinically effective in the treatment of endogenous depression in humans at daily doses of approximately 80 to 160 mg p.o. (Náhunek et al., Act. Nerv. Super Vol. 32, pages 230–231 (1990)).

The invention is based on the surprising discovery that 4-(7-bromo-5-methoxybenzo-furan-2-yl)piperidine (brofaromine) including its pharmaceutically acceptable salts has, in addition to their efficacy as antidepressants, a pronounced nootropic activity.

For example, a cerebral electroshock administered immediately after a learning experience (e.g. a passive avoidance task) erases memory of the preceeding experience. Brofaromine at doses of 0.3 and 3 mg/kg administered 1 hour before the learning trial and the cerebral electroshock significantly reduces the degree of amnesia induced by the shock, i.e. increases the time spent in the "dangerous" illuminated compartment of the experimental apparatus upon retest. At 30 mg/kg p.o., a positive trend can be observed (for results of such an experiment confer "Pharmacological Example 1 "). This anti-amnestic effect is typical for for nootropics (Mondadori et al., Clin. Pharmacol. Vol. 9, pages S27–S34 (1986)). In a comparative study with brofaromine and moclobemide using a similar design, significant anti-amnestic effects of brofaromine were found at doses of 0.03, 0.1, 1.0, 3.0 and 30 mg/kg p.o., whereas moclobemide showed an activity at a dose of 30 mg/kg p.o., only. This clearly indicates that the nootropic effect of brofaromine is independent of MAO inhibition and serotoninergic effects, because it occurs at much lower doses than either of these.

Furthermore, in a one-way passive avoidance test brofaromine, at doses of 0.3 and 3.0 mg/kg significantly improves acquisition performance of 27 months old rats, i.e. the treatment reduces the number of learning trials to reach the learning criterion of five consecutive successful avoidances. The mean number of avoidances found in animals treated with 3.0 mg/kg p.o. of brofaromine by was 10.2+1.8 as compared with the number 21.7±4.5 found in untreated control animals. Effects in this type of situations are typical for nootropics (Mondadori et al, loc. cit.).

Brofaroomine has positive effects on memory retrieval. Memory of a learning experience fades with time. Two month after having been exposed to a passive avoidance learning situation, only about 20 per cent of the animals remember, i.e. show behavioral changes indicative of retention. Accordingly, any improvement of retention performance induced by a treatment given one hour before before the test for retention can be interpreted in terms of an effect on memory retrieval (Mondadori and Etienne, Psychopharmacology Vol. 100, pages 301–307 (1990)).Experiment of this type are sensitive to the effects of a variety of nootropic compounds including also the Ca-antagonist nimodipine and the cholinesterase-blockers tactine and physiostigmine. Brohromine administered 1 hour before the retention test significantly prolonged step-through latencies of mice at doses of 0.3, 3.0 and 30 mg/kg p.o., whereas the MAO-A inhibitor moclobemide had no such effect. That means that the effect of brofaromine cannot be based on MAO inhibition. The low effective doses also indicate that serotoninergic effects cannot account for its effects.

On account of these properties, 4-(7-bromo-5-methoxybenzofuran-2-yl)piperidine and its pharmaceutically acceptable salts are excellently suitable to treat behavioral symptoms induced by neurodegenerative diseases like Alzheimer's disease, multi-infarct dementia or dementia of the Alzheimer type, and also the consequences of brain traumas or apoplexies.

The suitability of brofaromine for retarding the treatment of behavioral symptoms accompanying neurodegenerative disorders has been confirmed in an exploratory multiple crossover double blind study in non-depressed patients suffering from mild to moderate dementia. Prolonged treatment with daily doses of 50 mg (25 mg BID) improve cognitive functions by the ADAS cognitive subscale and behavior on IDQ and DBRI frequency significantly.

The active ingredients for nootropic medicaments proposed according to the invention may be administered enterally or parenterally, especially orally or intravenously. The recommended daily dose is, for example, from approximately 0.25 to approximately 1.5 mg/kg or from approximately 20 to approximately 100 mg/70 kg, preferably from approximately 0.5 to approximately 1.0 mg/kg or approximately from 35 to 70 mg/70 kg, which are advantageously be divided into 2 single doses of, for example, from approximately 15 to approximately 35 mg/70 kg, preferably from approximately 20 to approximately 30 mg/70 kg, for example, approximately 25 mg/70 kg.

The nootropic pharmaceutical compositions provided according to the invention are preferably pharmaceutical compositions in unit dose form for enteral, such as oral, also rectal, and parenteral administration to (a) warm-blooded animal(s), the compositions comprising the pharmacological active ingredient on its own or together with a pharmaceutically acceptable carrier.

The nootropic pharmaceutical compositions provided according to the invention comprise, for example, from approximately 10 % to approximately 80 %, preferably from approximately 20 % to approximately 60 %, active ingredient. Pharmaceutical compositions according to the invention for enteral or parenteral administration are, for example, compositions in unit dose form, such as dragées, tablets, capsules or suppositories, and also ampoules. They are prepared in a manner known per. se, for example by means of conventional mixing, granulating, confectioning, dissolving or lyophilizing processes. For example, pharmaceutical compositions for oral administration can be obtained by combining the active ingredient with solid carders, optionally granulating a resulting mixture, and processing the mixture or granules, if desired or necessary after the addition of suitable excipients, to form tablets or dragde cores.

Suitable carders are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and, if desired, disintegrators, such as the above-mentioned starches and also carboxymethyl starch, cross-linked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragde cores are provided with suitable, optionally enteric coatings, there being used inter alia concentrated sugar solutions, which may comprise gum arabic, talc, polyvinylpyrrolidone, polyethylene glycol and/or titanium dioxide, coating solutions in suitable organic solvents or solvent mixtures or, for the preparation of enteric coatings, solutions of suitable cellulose preparations, such as acetylcellulose phthal,ate or hydroxypropylmethylcellulose phthalate. Colorings or pigments may be added to the tablets or dragde coatings, for example for identification purposes or to indicate different doses of active ingredient.

Pharmaceutical compositions for oral administration are also hard gelatin capsules, and soft sealed capsules consisting of gelatin and a plasticizer, such as glycerol or sorbitol. The hard gelatin capsules may contain the active ingredient in the form of granules, for example in admixture with fillers, such as lactose, binders, such as starches, and/or glidants, such as talc or magnesium stearate, and optionally stabilistabilizers. In soft capsules the active ingredient is preferably dissolved or suspended in suitable liquids, such as fatty oils, paraffin oil or liquid polyethylene glycols, it likewise being possible to add stabilizers.

Suitable rectally administrable pharmaceutical compositions are, for example, suppositories that consist of a combination of the active ingredient with a suppository base. Suitable suppository bases are, for example, natural or synthetic triglycerides, paraffin hydrocarbons, polyethylene glycols or higher alkanols. It is also possible to use gelatin rectal capsules, which contain a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that comprise viscosity-increasing substances, for example sodium carboxymethylcellulose, sorbitol and/or dextran, and, if desired, stabilizers.

The following Examples serve to illustrate the invention; temperatures are given in degrees Celsius, pressures in mbar.

Pharmacological Example 1: Protection against the amnesiogenic effect of a cerebral electric shock in mice It is an empirical clinical fact that cerebral electric shock treatment leads to retrograde amnesia; the ability to remember events immediately before the electric shock is impaired. Neither the biochemical mechanism nor the nature of the psychological process affected by the treatment is known. However, there is virtually no doubt that the electric shock affects the recollection process in some way. The fact that the retrograde amnesia is time-dependent (the greater the period of time that has elapsed since the information was absorbed, the less pronounced is the effect) suggests an influence on a time-limited process, which most probably concerns fixing the memory pathway or consolidating the contents of the memory. It is therefore to be assumed that medicaments that facilitate fixing of the memory pathway have an advantageous effect on amnesia brought about by the electric shock, for example they shorten the period of time during which fixing of the memory pathway is impaired and thus reduce the extent of the amnesia. In the animal experiment, amnesia induced by an electric shock can be observed when the cerebral electric shock is applied within a few seconds following the learning process, which in the present case is a passive avoidance task.

Experimental arrangement

A larger cage compartment (35×20×10 cm) communicates with a smaller cage compartment (10×10×10 cm) by means of a sliding door. The smaller cage compartment is illuminated from above by means of a 100 Watt light bulb; the larger cage compartment is dark. The floor of both cage compartments consists of an electrically conductive grid.

Method

The test animals are placed individually in the illuminated cage compartment. Since mice have a natural preference for a dark environment, most of the test animals move spontaneously into the dark cage compartment. As soon as all the test animals are in that compartment, the sliding door is closed and an electric shock (1 mA, 5 sec) is administered to their feet.

The test animals are removed immediately, and 24 hours later they are again placed in the illuminated cage compartment. The period of time for which the test animals hesitate before moving into the dark cage compartment is measured. In general, most of the test animals remain in the illuminated cage compartment for the entire observation period (150 sec), which means that virtually all the test animals have mastered the learning task.

If a cerebral electric shock (14 mA, 0.2 s, 150 Hz) is administered immediately after the foot-shock phase of the learning process, the test animals' ability to remember the foot shock is impaired. 4-(7-Bromo-5-methoxybenzofuran-2-yl)piperidine in the form of the hydrochloride has a pronounced anti-amnesiogenic protective effect in this model when administered perorally 60 minutes prior to the cerebral electric shock.

| Measurement results: | | |
|---|---|---|
| Test compound | Time in illuminated cage compartment | Significance |
| 0.3 mg/kg p.o. active ing. | 25.9 s | p < 0.01 |
| 3.0 mg/kg p.o. active ing. | 38.9 s | p < 0.0002 |
| 30.0 mg/kg p.o. active ing. | 14.5 s | n.s. |
| Vehicle on its own | 10.4 s | |

Conclusion

The active ingredient is effective at 0.3, 1.0 and 3.0 mg/kg p.o.. The most pronounced activity is to be observed at 3.0 mg/kg p.o.; the average time spent in the illuminated cage compartment in that case is 38.8×7.9 sec ($p > 0.0002$). At 30.0 mg/kg p.o., a positive trend is observed. As compared with the time spent in the illuminated cage compartment following administration of the vehicle on its own (10.4 s), this corresponds to a statistically highly significant increase, by a factor of 3.7.

Pharmacological Example 2: Action in the case of chronic treatment on the learning ability of aged rats A certain deterioration in higher intellectual functions, noticeable especially in the storage and utilization of information, is a feature and a consequence of the natural ageing process in humans and animals. In animals, a decline in the ability to gather and utilize information can be observed. Elderly test animals are therefore useful test subjects for investigating age-related cognitive malfunctions, and especially for studying the effect of active ingredients for medicaments on age-related memory dysfunctions.

Experimental arrangement

The experimental arrangement consists of two identical cage compartments A and B (each measuring 20×20×30 cm) which communicate by means of a door (12×16 cm) and are provided with electrically conductive floor grids. The learning test consists in placing the test animal in cage compartment A and, after 10 seconds, subjecting it to an electric shock to its feet. The test animal can avoid this by moving into cage compartment B. Training in this active one-way avoidance task is continued until the test animal is able to avoid the electric shock in this manner five times in succession.

Method

Elderly rats (age at start of test: 27 months) are treated daily perorally with 0.3, 1.0, 3.0 and 30 mg/kg of the test compound. The vehicle is administered to a control group. 60 minutes after the treatment, the test animals are subjected to the above training. A further learning attempt takes place 4 hours later.

| Measurement results: | | |
|---|---|---|
| Test compound | Number of learning attempts | Significance |
| 0.3 mg/kg p.o. active ing. | 15.6 ± 2.6 | p < 0.05 |
| 3.0 mg/kg p.o. active ing. | 10.2 ± 1.8 | p < 0.02 |
| Vehicle on its own | 21.7 ± 4.5 | |

Conclusion

Doses of 0.3 and 3.0 mg/kg p.o. of the active ingredient bring about a statistically significant reduction, to 47 % of the control value, in the number of learning attempts required to learn the active avoidance task.

Clinical Example

Investigation of the effects of brofaromine in patients suffering from mild to moderate dementia. The effects of brofaromine in patients suffering from mild to moderate dementia were studied in an exploratory multiple crossover double blind study in patients with mild to moderate dementia. The object was to obtain preliminary information on the safety of the compound, and on the drug's effects on behavior, mood, activities of daily living (ADL) and cognitive performance.

Study design

The trial consisted of two phases. A first single blind placebo run-in one week phase was used to evaluate the competence of the caregivers and to familiarize, both, patients and caregivers with the daily tasks required by the protocol.

The second phase was a randomized placebo controlled, double-blind phase (24 weeks) involving three pairs of treatment periods; each pair consisting of four weeks on active and four weeks on placebo. Patients were randomized to receive either 25 or 50 mg bid of brofaromine during the three pairs. Whether patients received drug or placebo in each pair was determined by randomization. No placebo wash-out period was included between the treatment pairs, allowing treatment periods of eight weeks. The patients were also randomized to have their visits performed in the Memory Clinic or in their homes.

Outcome measures included assessments of behavior, mood, ability to perform instrumental activities of daily living, assessment of daily living activities, and cognitive functioning using various instruments and the Alzheimer's Disease Assessment Scale. Behavioral and functional assessments were done by the caregiver weekly at home.

Patients

Patients had to meet the following inclusion criteria: aged over 40, impairment in at least two of the following function: memory, abstraction, attention, judgement, learning, orientation, language, constructional difficulty, or activities of daily living. No delirium, SMMSE score of 12–25, Geriatric Depression Scale (GDS) rating score of less than 11 (excludes depression, Reisberg Global Deterioration Scale (RGDS) score of 3–5).

Excluded were patients with a history of significant behavioral symptomatology, of long-term psychoactive drug use, reversible dementias, and patients with difficulties to cooperate in the study.

Results

The results are summarized in the following Table 1, wherein the variables have the significancies indicated in "Legend":

TABLE 1

COMPARISON BETWEEN PATIENTS WHO CONTINUED ON EXTENTION MEDICATION AND THOSE WHO DID NOT.

| OUTCOME MEASURE | CHANGE (SD) EX-TENSION[1] | CHANGE (SD) OTHERS[3] | DIFFER-ENCE[3] | p[4] |
|---|---|---|---|---|
| ADAS-noncog | 0.52 (4.03) | −0.37 (2.35) | 0.89 | 0.423 |
| IDQ | 1.89 (2.14) | −0.64 (1.90) | 2.53 | 0.002 |
| DBRI-freq | 2.37 (6.27) | −1.28 (3.94) | 3.65 | 0.054 |
| DBRI-reac | 2.21 (2.94) | −0.25 (4.57) | 2.46 | 0.169 |
| SMMSE | −0.59 (1.41) | −1.01 (1.63) | 0.42 | 0.497 |
| ADAS-cog | 1.28 (2.92) | −1.47 (2.74) | 2.75 | 0.016 |
| TAKE-HOMES | | | | |
| IDQ | 1.92 (2.04) | −0.22 (1.34) | 2.14 | 0.003 |
| DBRI-freq | 5.36 (3.96) | 0.42 (2.41) | 4.94 | 0.001 |
| DBRI-reaq | 5.52 (3.59) | 0.31 (2.16) | 5.21 | 0.001 |
| LAWTON | 1.00 (1.63) | −0.08 (1.17) | 1.08 | 0.055 |
| SPQ | 0.50 (1.58) | −0.88 (1.92) | 1.38 | 0.082 |

[1]Main pair difference for patients who continued on extension (n = 9)
[2]Main pair difference for patients who did not continue on extension (n = 25)
[3]Difference between both groups; a positive difference favors the group on extension
[4]Two-tailed t-tests Legend

*ADAS*: Alzheimer's Disease Assessment Scale. An instrument to assess the severity of cognitive and non-cognitive behavioral dysfunctions characteristic of persons with Alzheimer's disease. The total score is arrived at after evaluations of, both, the caregiver (non-cognitive behavior) and the patient (cognitive behavior).

*IDQ*: Individual Dementia Questionnaire. A selection of five areas of dysfunction experienced by patients considered by the caregiver to be most important. Rated by the caregiver using a seven point Likert scale.

*DBRI*: Dysfunctional Behavior Rating Instrument. Measures the frequency and the severity of problems with dysfunctional behavior of demented patients.

*SMMSE*: Short, standardized mental status examination to determine the severity of the cognitive impairment.

*LAWTON*: Scale to rate the patients performance in activities of daily living (ADL) i.e. toileting, feeding, dressing etc.

*GDS*: Geriatric Depression Scale. Depression scale specifically for the elderly. 30 questions.

*RGDS*: Reisberg Global Deterioration Scale. A seven point evaluation of the patient's general state: 1=complete independence, 7=complete dependence.

*SPQ*: Sleep Problem Questionnaire.

Discussion

Similar to other studies with e.g. nootropic or cholinergic compounds only a limited number of patients responded to the treatment. Accordingly, the caregivers impression and the decision to chose brofaromine in the extention medication phase was considered to be an important input. Nine patients out of a total of 34 were elected to continue on with the extension medication after the end of the 6 months double blind trial. Eight of these nine patients belonged to the group of patients with the greatest number of positive outcomes. One caregiver chose placebo.

A separate analyses of these patients on extension medication vs. the others revealed the following: the group on extention had a statistically significant improvement in cognition by the ADAS cognitive subscale compared to the others. Behavior was also significantly improved on two clinical instruments (IDQ and DBRI-frequency). The take home versions of those Behavior instruments achieved very high levels of significance (IDQ p<003, DBRI-freqency p<0.001 ). ADL (Lawton) and caregiver burden (DBRI reaction) showed also positive effects on the take home versions. All outcome measures were in the positive direction. TABLE 1 gives an overview over the results.

A four months crossover analysis of the Lawton ADL scores shows that the low dose 25 mg bid of brofaromine was superior to the high dose (50 bid), improvement 1.78, p<0.03. This analysis could be done due to the fact that some patients (by chance) had a 2 months period of continuous treatment. The results clearly confirm the predictions made on the basis of animals experiments that the beneficial effect in patients might appear at doses much lower than those necessary for an antidepressant effect (150 mg/day) and a complete blockage of MAO A. Accordingly, the effective clinical dose would be expected to range from 10 mg bid to 50 mg bid.

It is important to understand, that under similar experimental conditions, neither oxiracetam (Molloy et al, J. Clin. and Experimental Gerontol. 14, 217–233, 1992) nor tacrine (Molloy et al. Can. Med. Assoc. J. 144, 29–34, 1991) were found to be efficacious. Moreover, the results clearly differ from clinical results with moclobemide where non-depressed Alzheimer patients showed no effect. Accordingly, MAO A inhibition alone cannot account for the observed clinical effects. Similarly, serotoninergic effects cannot account for the clinical effects, since serotoninergic effects occur at doses higher than those inhibiting MAO A (Waldmeier, Progr. Neuro-Psychopharmacol. & Biol. Psychiatr. 1993, 183–198).

Formulation Example 1

Tablets, each comprising 200 mg of 4-(7-bromo-5-methoxy-benzofuran-2-yl)piperidine or of a salt, for example the hydrochloride, thereof, can be prepared as follows:

| Composition (10 000 tablets) | |
|---|---|
| active ingredient | 2000.0 g |
| lactose | 500.0 g |
| potato starch | 352.0 g |
| gelatin | 8.0 g |
| talc | 60.0 g |
| magnesium stearate | 10.0 g |
| silica (highly disperse) | 20.0 g |
| ethanol | q.s. |

The active ingredient is mixed with the lactose and 292 g of potato starch, and the mixture is moistened with an ethanolic solution of the gelatin and granulated through a sieve. After drying, the remaining potato starch, the magnesium stearate, the talc and the silica are mixed in and the mixture is compressed to form tablets which each weigh 295.0 mg and comprise 50.0 mg of active ingredient, and which may, if desired, be provided with dividing notches for finer adjustment of the dose.

Formulation Example 2

Film-coated tablets, each comprising 400 mg of 4-(7-bromo-5-methoxybenzofuran-2-yl)piperidine or of a salt, for example the hydrochloride, thereof, can be prepared as follows:

| Composition (for 1000 film-coated tablets) | |
|---|---|
| active ingredient | 400.0 g |

-continued

| Composition (for 1000 film-coated tablets) | |
| --- | --- |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed, and the mixture is moistened with a paste, prepared from 15 g of corn starch and water (with heating), and granulated. The granules are dried, and the remaining corn starch, the talc and the calcium stearate are added and mixed with the granules. The mixture is compressed to form tablets (weight: 580 mg), which are coated with a solution of the hydroxypropylmethylcellulose and the shellac in methylene chloride; final weight of each film-coated tablet: 583 mg.

Formulation Example 3

Hard gelatin capsules, each containing 500 mg of 4-(7-bromo-5-methoxybenzofuran-2-yl)piperidine or of a salt, for example the hydrochloride, thereof can be prepared, for example, as follows:

| Composition (for 1000 capsules) | |
| --- | --- |
| active ingredient | 500.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilized active ingredient through a sieve having a mesh size of 0.2 min. The two components are mixed intimately. Then, first the lactose is added through a sieve having a mesh size of 0.6 mm and then the microcrystalline cellulose through a sieve having a mesh size of 0.9 mm. The mixture is mixed intimately again for 10 minutes. Finally, the magnesium stearate is added through a sieve having a mesh size of 0.8 mm. After further mixing for 3 minutes, hard gelatin capsules of a suitable size are each filled with 790 mg of the resulting formulation.

Formulation Example 4

A 5 % injection or infusion solution of 4-(7-bromo-5-methoxy-benzofuran-2-yl)piperidine or of a salt, for example the hydrochloride, thereof can be prepared, for example, as follows:

| Composition (for 1000 or 400 ampoules) | |
| --- | --- |
| active ingredient | 125.0 g |
| sodium chloride | 22.5 g |
| phosphate buffer pH = 7.4 | 300.0 g |
| demineralized water | ad 2500.0 ml |

The active ingredient and the sodium chloride are dissolved in 1000 ml of water and filtered through a microfilter. The buffer solution is added, and the mixture is made up to 2500 ml with water. To prepare unit dose forms, 1.0 or 2.5 ml are introduced into each glass ampoule, which then contains 50 or 125 mg, respectively, of active ingredient.

What is claimed is:

1. A method of retarding the degeneration of nerve cells that accompanies degenerative nerve disorders and of treating cerebral insufficiency, which comprises administering a therapeutically effective amount of 4-(7-bromo-5-methoxy-benzofuran-2-yl)piperidine (brofaromine) of formula I

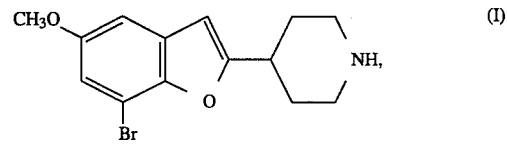

or of a pharmaceutically acceptable salt thereof to a warm-blooded organism in need of such treatment.

2. A method of treatment as claimed in claim 1 wherein a daily dose of 20 to 100 mg is administered.

3. A method of treatment as claimed in claim 1 wherein a daily dose of 35 to 70 mg is administered.

4. A method of treatment as claimed in claim 1 wherein a daily dose of 20 to 30 mg is administered.

5. A method of treatment as claimed in claim 1 wherein the daily dose is divided into two single doses.

* * * * *